United States Patent [19]

Connolly et al.

[11] Patent Number: 5,708,692
[45] Date of Patent: Jan. 13, 1998

[54] MEASUREMENT SYSTEM FOR CHROMIUM CONTENT IN CHROMIZED LAYERS AND THE LIKE

[75] Inventors: Dennis Connolly, Alliance; Walter R. Mohn, North Canton; Bart A. Stuchell, Alliance, all of Ohio

[73] Assignee: The Babcock & Wilcox Company, New Orleans, La.

[21] Appl. No.: 758,806

[22] Filed: Dec. 3, 1996

[51] Int. Cl.⁶ .................................. G01N 23/223
[52] U.S. Cl. ............................. 378/45; 378/44
[58] Field of Search ................. 378/45, 44, 49, 378/50, 51, 53, 54, 57, 58, 59, 60, 86, 88, 89

[56] References Cited

U.S. PATENT DOCUMENTS 4,692,935  9/1987  Kumakura et al. ............... 378/45 X
5,081,658  1/1992  Imai et al. ........................ 378/45
5,113,421  5/1992  Gignoux et al. ................ 378/45 X

*Primary Examiner*—David P. Porta
*Attorney, Agent, or Firm*—Robert J. Edwards; Eric Marich

[57] ABSTRACT

A method and apparatus for measuring a target analyte diffused in a wall of a metal member provides a sample of the metal member which is cut to progressively reduce a wall thickness of the sample from zero at a first point on the sample to a selected depth at a second point on the sample. An x-ray analyzing system having an analyzing slot is moved past the sample between the first and second points. Data from the x-ray analyzing system during the translation of the sample is collected to analyze the analyte content.

12 Claims, 2 Drawing Sheets

MEASUREMENT SYSTEM FOR CHROMIUM CONTENT IN CHROMIZED LAYERS AND THE LIKE

FIELD AND BACKGROUND OF THE INVENTION

The present invention relates in general to a process for analyzing metal tubes, and in particular, to a new and useful system and method for measuring the content of a target analyte such as a metallic diffusion coating, in a wall of a metal member.

Chromizing is a process used to produce a chromium rich surface diffusion coating on metals. This process is used on boiler components (i.e., tubes, pipes, etc.) to provide an internal or external surface which is resistant to exfoliation (i.e., high temperature oxidation with subsequent breaking away or loss of the oxide layer). Chromizing has been widely used throughout industry for many years.

For good process control, a method is needed to characterize the chromium diffusion profile as a function of depth from the outer surface. Two methods which have been used for this purpose are optical microscopy and electron probe microanalysis (EPMA) applied to metallographically prepared cross sectional specimens. The present invention provides an alternative method of characterization which is more rapid and which may be adaptable to an on-site process in the factory setting.

SUMMARY OF THE INVENTION

The present invention is applied to a chromized tube specimen as an example, but the method is applicable to other types of metal samples with appropriate modification of sample preparation and positioning in an x-ray analyzer. To measure the chromium content in the surface layer of a chromized tube, the surface is cut in a tapered fashion on a lathe such that the thickness removed varies linearly from zero to some desired depth (for example 0.016") over a certain length of the tube (for example 2").

Accordingly, an object of the present invention is to provide a system and method for measuring a target analyte diffused in a wall of a metal member, comprising providing a sample of the metal member, cutting a surface of the sample to progressively reduce a wall thickness of the sample from zero at one point on the sample, to a selected depth at another point on the sample, providing an x-ray analyzing system having an analyzing slot, translating and rotating the sample between the first and second points and then past the slot, and accumulating data from the x-ray analyzing system during the rotation and translation of the sample.

A further object of the invention is to provide a method and system for analyzing a metal sample which is simple in design, rugged in construction and economical to manufacture.

The various features of novelty which characterize the invention are pointed out with particularity in the claims annexed to and forming a pan of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
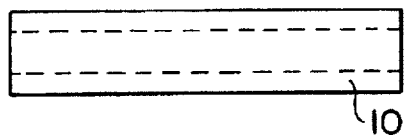
FIG. 1 is a side elevational view of a sample of a metal tube to be analyzed according to the present invention.

Referring to the drawings generally, wherein like numerals represent the same or functionally similar elements throughout the several drawings, and to FIG. 1 in particular, the invention embodied therein comprises a system and method for measuring a target analyte in the wall of a metal member.

An example of the invention analyzes chromium as the target analyte in the wall of a metal tube. FIG. 1 illustrates a two inch long section of tube 10 having a relatively thick wall thickness (e.g. about ⅛").

Figure 2:
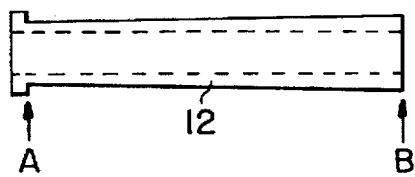
FIG. 2 is a view similar to FIG. 1 of the sample after it has been machined.

Another step of the present invention illustrated in FIG. 2 is the progressive machining away of an outer tapered area along the sample, progressively from a point B where nothing is removed from the wall thickness, to a point A where, for example, 0.016" to 0.020" of wall has been removed. This is the cut sample or specimen 12.

In this way, the profile of the depth of the sample into which chromium was diffused, can be obtained.

Figure 3:
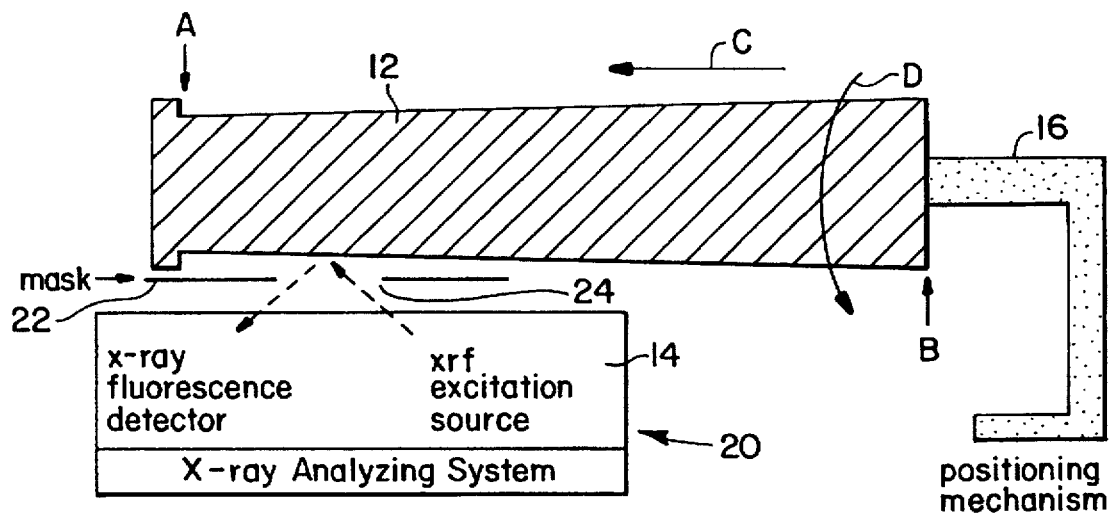
FIG. 3 is a side elevational view of a system of the invention for use in analyzing the cut sample.

FIG. 3 illustrates the set up of the invention. Sample 12, which is the cut version of the original sample 10, is mounted in a positioning and/or movement system schematically illustrated at 16.

The cut specimen 12 is positioned with its cut portion over the measuring head 14 (excitation source and fluorescence detector) of an x-ray fluorescence (XRF) analyzing system 20. Between the measuring head and the sample, a masking material or mask 22 with a narrow slot 24 (for example, 0.5"×0.05") is positioned in a way that the slot 24 opening can be moved along the length of the cut section of the specimen, or the specimen 12 can be moved in the direction of arrow C, past the slot. In this way, measurements can be made at discrete depths along the tapered cut between deepest cut area A and zero cut area B. The circumferential uniformity of the chromium content at a particular depth may be evaluated by making measurements as the tube specimen 12 is rotated adjacent the slot 24 in the direction of arrow D. The masking material confines the exposed section of the specimen to the open area of the slot. In preliminary experiments, ⅛" plexiglass was shown to be an effective masking material for mask 22.

Using portable x-ray equipment 20, an analyzing station may readily be installed and operated at the chromizing site to integrate quality control functions in the manufacturing process.

The method, including a sample preparation and analysis, may be automated to facilitate continuous operation in the factory setting.

The above descriptions used a chromized tube as an example. The method could as well be applied to metal specimens of other geometries (i.e., sheet, bars, etc.). Additionally, since the x-ray analyzing system is of the energy dispersive type, metals other than chromium could serve as the target analyte so other metallic diffusion coatings may be evaluated similarly. Multicomponent coatings are equally amenable to this method.

A comparison of chromium diffusion profiles of the invention, determined by x-ray Fluorescence Spectrometry (XRF) and by Electron Probe Microanalysis (EPMA) was made. The results are shown in FIG. 4.

The longitudinal specimen 10 was cut from a chromized tube sample (reported to have a 14 mil chromized coating). The specimen was machined with a 16 mil linear taper over a 2" length to form the specimen 12 and to allow chromium concentrations to be measured with XRF at a specific depths throughout the thickness of the chromized coating. Measurements were taken along the specimen at two peripheral locations by using a Kevex 770 XRF, recently upgraded with Pentium PC control employing IXRF Systems software.

To characterize the chromized coating and to obtain a comparison of the XRF diffusion profile with an EPMA diffusion profile, an adjacent transverse specimen was cut from the chromized tube sample and metallographically prepared. Optical micrographs (100×) of the specimen revealed a dense chromium layer with good substructural integrity, although some light porosity was observed immediately below a slightly irregular surface. Rational measurements using a certified Nikon Measurescope 20 (B&W No. 0890252) confirmed a chromium layer thickness of 14 mils and showed a decarburized depth of 20 mils. Measurements of chromium concentration were taken by EPMA at 6 micrometer intervals, beginning at the O.D. surface (within the primary chromium carbide layer) and ending at the inner boundary (just outside of the secondary chromium carbide layer).

Figure 4:
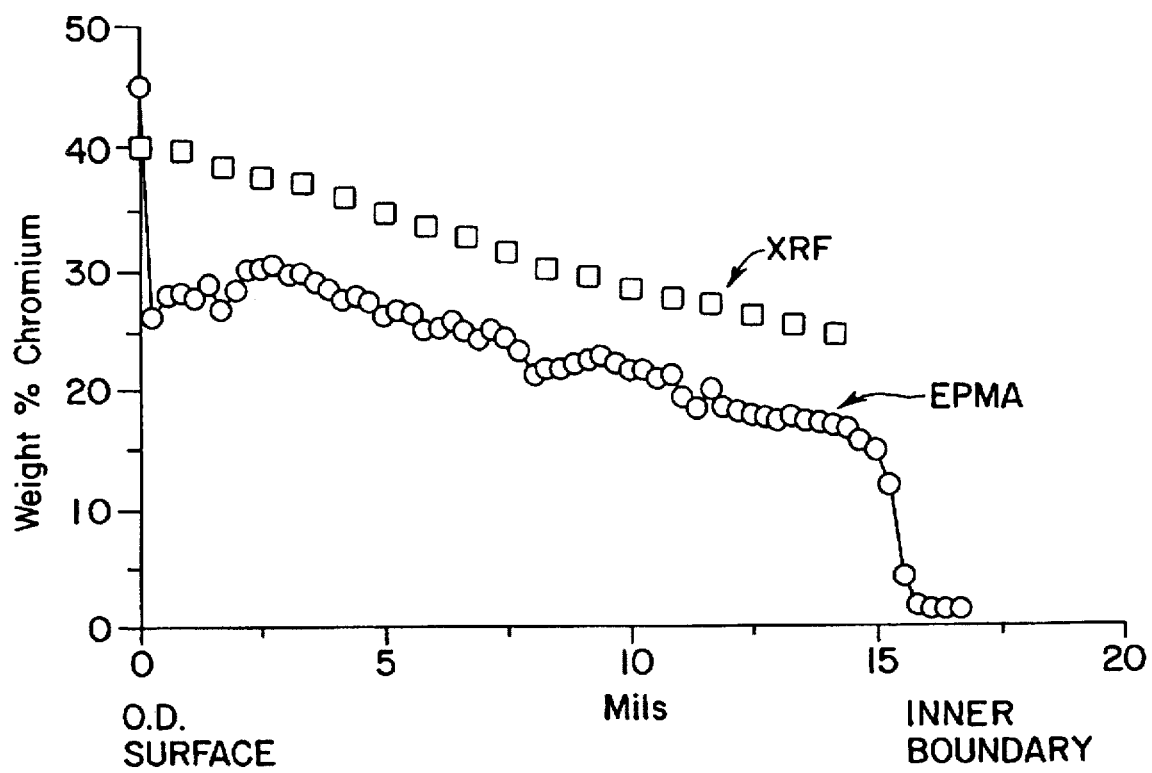
FIG. 4 is a graph comparing the results of the invention to another analyzing technique.

Chromium diffusion profiles determined by XRF and by EPMA were plotted on the same graph for comparison (see FIG. 4). Results show that the profiles are similar, but chromium concentration determined by XRF is generally about 5 weight percent higher than that determined by EPMA. This difference is believed to be due to the relatively larger masked beam size used in XRF technique.

While a specific embodiment of the invention has been shown and described in detail to illustrate the application of the principles of the invention, it will be understood that the invention may be embodied otherwise without departing from such principles.

We claim:

1. A method for measuring a target analyte diffused in a wall of a metal member, comprising:

providing a sample of the metal member;

cutting a surface of the sample to progressively reduce a wall thickness of the sample from zero at a first point on the sample to a selected depth at a second point on the sample;

providing an x-ray analyzing system having an analyzing slot;

translating the sample between the first and second points, and past the slot; and accumulating data from the x-ray analyzing system during the translation of the sample.

2. The method according to claim 1, wherein the analyte comprises a metal.

3. The method according to claim 2, wherein the analyte metal is chromium.

4. The method according to claim 3 wherein the metal member is a tube, the method including rotating the tube past the slot.

5. The method according to claim 2 wherein the metal member is a tube, the method including rotating the tube past the slot.

6. The method according to claim 1 wherein the metal member is a tube, the method including rotating the tube past the slot.

7. The method according to claim 6 including moving the tube linearly past the slot and rotating the tube for producing a profile of the entire wall of the tube between the points.

8. The method according to claim 7 wherein the analyte is a metal.

9. The method according to claim 8 wherein the analyte metal is chromium.

10. A system for measuring a target analyte diffused in a wall of a metal member, comprising:

a sample of the metal member which has a surface with a wall thickness that has been cut down from zero at a first point on the sample, to a selected depth at a second point on the sample;

an x-ray analyzing system having an analyzing slot; and means for translating the sample between the first and second points and past the slot for accumulating data from the x-ray analyzing system during the translation of the sample.

11. The system according to claim 10 including means for rotating the sample and linearly translating the sample, the sample being a tube.

12. The system according to claim 11 wherein the tube has a chromium diffusion layer in the wall thickness.

* * * * *